United States Patent
Efinger et al.

(10) Patent No.: US 8,672,921 B2
(45) Date of Patent: Mar. 18, 2014

(54) FLEXIBLE HOLLOW SHAFT FOR A MEDICAL INSTRUMENT

(75) Inventors: Andreas Efinger, Rietheim (DE); Rainer Hermle, Gosheim (DE)

(73) Assignee: Karl Storz GmbH & Co. KG (DE)

( * ) Notice: Subject to any disclaimer, the term of this patent is extended or adjusted under 35 U.S.C. 154(b) by 1594 days.

(21) Appl. No.: 11/686,870

(22) Filed: Mar. 15, 2007

(65) Prior Publication Data
US 2007/0219539 A1   Sep. 20, 2007

(30) Foreign Application Priority Data
Mar. 15, 2006   (DE) .......................... 10 2006 013 979

(51) Int. Cl.
*A61B 17/00* (2006.01)

(52) U.S. Cl.
USPC .............................................. 606/1; 606/180

(58) Field of Classification Search
USPC ................................. 606/1, 80, 180
See application file for complete search history.

(56) References Cited

U.S. PATENT DOCUMENTS

| | | | | |
|---|---|---|---|---|
| 4,706,659 A | | 11/1987 | Matthews et al. ............. | 128/92 |
| 4,763,548 A | * | 8/1988 | Leibinger et al. ............ | 81/453 |
| 4,960,410 A | * | 10/1990 | Pinchuk ..................... | 604/96.01 |
| 5,405,348 A | * | 4/1995 | Anspach et al. ............. | 606/80 |
| 5,431,660 A | * | 7/1995 | Burke ......................... | 606/104 |
| 5,462,548 A | * | 10/1995 | Pappas et al. ............... | 606/80 |
| 5,472,439 A | * | 12/1995 | Hurd ........................... | 606/1 |
| 5,690,660 A | | 11/1997 | Kauker et al. ............... | 606/180 |
| 7,287,449 B2 | * | 10/2007 | Abel et al. .................. | 81/177.2 |
| 2002/0029055 A1 | | 3/2002 | Bonutti ........................ | 606/170 |
| 2002/0038129 A1 | | 3/2002 | Peters et al. ................ | 606/167 |
| 2004/0097932 A1 | * | 5/2004 | Ray et al. .................... | 606/61 |
| 2005/0090849 A1 | * | 4/2005 | Adams ......................... | 606/180 |
| 2005/0177168 A1 | | 8/2005 | Brunnett et al. ............. | 606/80 |
| 2006/0048613 A1 | * | 3/2006 | Abel et al. ................... | 81/177.2 |
| 2006/0079735 A1 | * | 4/2006 | Martone et al. .............. | 600/104 |

FOREIGN PATENT DOCUMENTS

| | | |
|---|---|---|
| DE | 101 07 156 | 5/2005 |
| EP | 0 191 630 | 6/1991 |
| EP | 1 382 307 | 1/2004 |
| EP | 1 410 765 | 4/2004 |
| EP | 0 986 989 | 4/2005 |
| EP | 1 598 023 | 11/2005 |

OTHER PUBLICATIONS

European Search Report, Sep. 24, 2007, 11 Pages.

* cited by examiner

*Primary Examiner* — Bill Thomson
*Assistant Examiner* — Jeffrey Lipitz
(74) *Attorney, Agent, or Firm* — St. Onge Steward Johnston & Reens LLC

(57) ABSTRACT

A flexible shaft to be received in a curved shank of a medical instrument has a hollow shaft having a wall with cuttings therein such that said hollow shaft can also transmit rotary forces in a curved state. Said hollow shaft has a proximal end for coupling to a drive mechanism of a medical instrument and a distal end on which a tool is arranged. In view of tension relief a body extending through an inside of said hollow shaft from said distal end to said proximal end is provided, said body is flexible but is axially inextensible and axially incompressible. In terms of pressure relief said distal end of said hollow shaft is provided with a limit stop which interacts with a limit stop on said medical instrument in such a way that a compression of said hollow shaft beyond a certain extend is blocked.

11 Claims, 2 Drawing Sheets

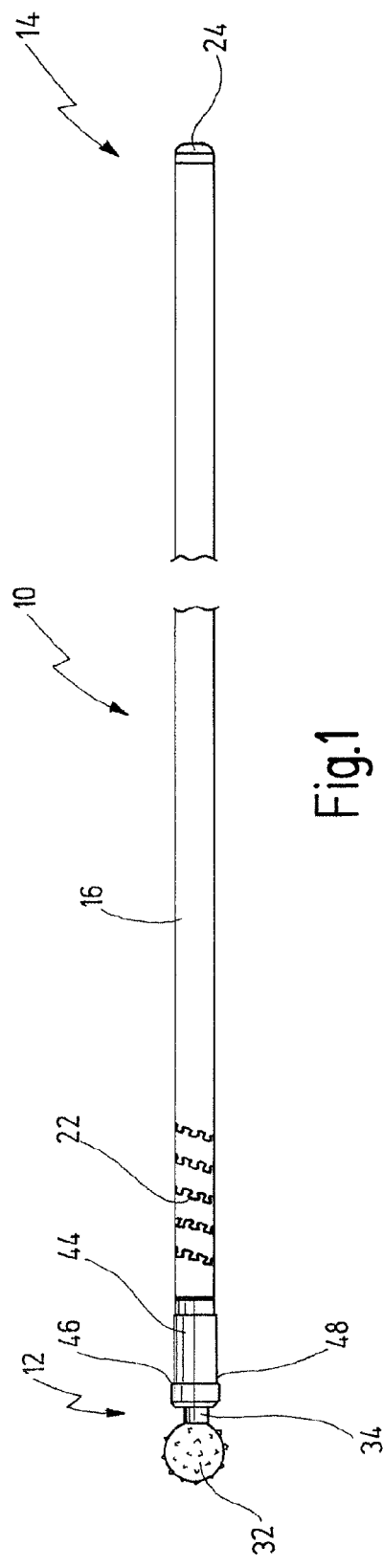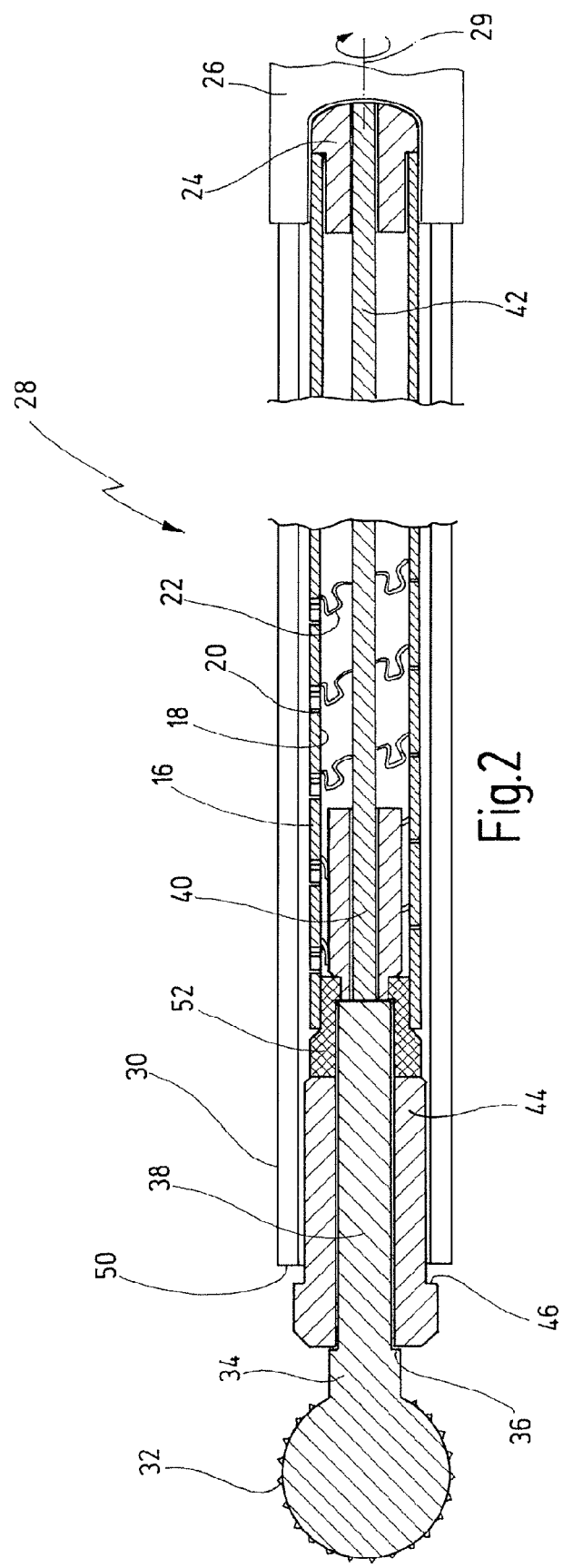

FLEXIBLE HOLLOW SHAFT FOR A MEDICAL INSTRUMENT

BACKGROUND OF THE INVENTION

The invention relates to a flexible hollow shaft to be received in a curved shank of a medical instrument, A surgical instrument having a flexible hollow shaft of this kind is known from EP 0 986 989 A1.

The flexibility of the hollow shaft means that the instrument or its shank can have a curved design. The flexible hollow shaft is received in the curved shank and its proximal end is connected to a drive mechanism which rotates the hollow shaft in the curved shank. At the distal end, the hollow shaft is provided with a tool, for example with a cutting edge or with a milling head. The distal end of the hollow shaft comes to lie freely rotatably in the distal end area of the curved instrument shank.

In the aforementioned EP 0 986 989 A1, the tool is designed as a cutting edge that is used to remove tissue.

DE 101 07 156 A1 discloses a medical instrument in which the tool is designed as a milling head that protrudes from the distal end of the curved instrument shank.

The wall of the hollow shaft is provided with a large number of cuttings, by which the flexibility is achieved. These openings consist, for example, of cuttings which are made in a meandering formation in the wall and which extend along a helical line. In this way, with a curved and rotating hollow shaft, it is possible for the cuttings on the outer face of the curvature to widen slightly.

In practical application, tensile forces and/or compressive forces act on the tool.

In the case of a milling head, for example as used in operations on the frontal sinuses, compressive forces occur when the milling head encounters a bone site and the operating surgeon pushes the instrument sharply against this bone site. Tensile forces may occur if the milling head has worked its way into the bone and an attempt is made to withdraw the instrument, such that the milling head catches on the bone.

Similar compressive loads/tensile loads occur in the case of cutting edges that become caught on tissue or cartilage.

In practical use, it has now been found that the flexible hollow shaft is able to take up tensile and/or compressive loads by virtue of its construction, i.e. the hollow shaft can be slightly extended or compressed. In these states, however, the hollow shaft turns no longer round with the curvature of the curved shank, but bulges slightly outward and strikes against the inside face of the curved shank, as a result of which undesired vibrations occur that make handling of the medical instrument difficult.

It is therefore object of the present invention to remedy this situation and to provide measures that prevent such undesired vibration or outward deflection of the hollow shaft.

SUMMARY OF THE INVENTION

In terms of tension relief this object is achieved by a flexible shaft to be received in a curved shank of a medical instrument, comprising a hollow shaft having a wall with cuttings therein such that said hollow shaft can also transmit rotary forces in a curved state, wherein said hollow shaft has a proximal end for coupling to a drive mechanism of a medical instrument and a distal end on which a tool is arranged. A body extends through an inside of said hollow shaft from said distal end to said proximal end of said shaft, that body is flexible but is axially inextensible and axially incompressible.

This measures have the advantage that this body arranged in the interior of the hollow shaft counteracts extension caused by tensile forces and thus ensures tension relief. Since this body is made flexible, it is able to follow the curvature of the hollow shaft. By being designed as an incompressible body, a certain degree of pressure relief is also provided which however, because of the flexibility of the body and because of the curved state, acts only to a certain extent but is nonetheless present.

In terms of pressure relief, this object is achieved by a flexible shaft to be received in a curved shank of a medical instrument, comprising a hollow shaft having a wall with cuttings therein such that the hollow shaft can also transmit rotary forces in a curved state, wherein said hollow shaft has a proximal end for coupling to a drive mechanism of a medical instrument and a distal end on which a tool is arranged. The distal end of the hollow shaft is provided with a limit stop which interacts with a limit stop on said medical instrument in such a way that a compression of said hollow shaft beyond a certain extend is blocked.

This measure has the advantage that pressure relief is obtained by the limit stop being in operative connection with a limit stop on the medical instrument, such that compression of the hollow shaft is blocked and the compressive forces are transmitted via the limit stop at the distal end of the hollow shaft to the limit stop on the medical instrument.

In an embodiment, a body which is flexible, but which is axially inextensible and axially incompressible, is present in the hollow shaft in addition to the limit stop.

This measure, in combination with the limit stop, has the advantage of ensuring both sufficient tension relief and also pressure relief.

Depending on what loads the hollow shaft is exposed to during practical use, it is within the scope of the invention to obtain the tension relief only via the inextensible and incompressible body in the interior, which also provides a certain pressure relief, or, if it is pressure relief that is predominantly wanted, to use the construction with the limit stop, or, if both relief forms are desired, to use the combination of limit stop and inextensible and incompressible body.

In an embodiment of the invention, the body is designed as a wire.

This measure has the advantage that a wire constitutes a very slender element that can be received in the interior of a hollow shaft that is also very thin. Such a wire has sufficient flexibility to be able to follow the movements of the hollow shaft. At the same time, the wire material is sufficiently strong to ensure tension relief, since such a wire is able to withstand considerable tensile forces without deformation in the sense of a longitudinal extension.

In another embodiment of the invention, the limit stop at the distal end is arranged on a sleeve which is mounted rotatably on the hollow shaft.

This measure has the advantage that the sleeve, when its limit stop comes to lie on the limit stop on the instrument, then remains fixed in position and can accordingly transmit the compressive forces, while the hollow shaft, as before, is able to rotate in the sleeve, such that functioning is fully maintained even in such a case of pressure relief.

In another embodiment of the invention, the limit stop is designed as a shoulder.

This measure has the advantage that, even with very small structural parts having diameters of a few millimeters, such a shoulder provides a sufficiently large surface area for force transmission, in order to provide effective pressure relief.

In another embodiment of the invention, the sleeve is mounted in an axially movable manner on the distal end.

This measure has the advantage that the sleeve has a certain axial play, so that in normal operation, when no pressure relief exists, it is received loosely in the distal end area of the curved shank and is freely rotatable around the hollow shaft, but that the limit stop comes into action after a certain axial displacement. This also opens up the possibility of permitting a certain degree of compression depending on the length of the hollow shaft, and of bringing the limit stop into engagement only when this permitted degree of compression is exceeded.

In another embodiment of the invention, the tool at the distal end is connected to the proximal end via the body.

This measure has the advantage that the tension relief and/or pressure relief can be obtained using only a small number of structural parts, namely by means of the wire-shaped body extending between the proximal end and the tool at the distal end.

In another embodiment of the invention, the cuttings of the hollow shaft are designed as a slit which winds in the shape of a helical line.

This measure, known per se, has the advantage that a particularly flexible hollow shaft is created.

In another embodiment of the invention, the slit winding in a helical line is designed as a slit with a meandering configuration.

This measure, also known per se, has the advantage that the hollow shaft, even if relatively long and thin, is excellent at transmitting rotary forces. Such a hollow shaft can be drawn apart quite easily, which means that the tension relief is necessary, and especially effective, particularly in the case of such slits with a meandering configuration.

In another embodiment of the invention, spacers are provided which keep the body inside the hollow shaft at a radial distance from the wall of the latter.

This measure has the advantage that the body is maintained at a distance from the inside face of the hollow shaft, such that, for example at high speeds of rotation and with the hollow shaft curved, it does not knock or run out of true.

In another embodiment of the invention, the spacers are designed in such a way that media in the interior of the hollow shaft can be transported in the axial direction.

During the use of the hollow shafts, their interior is utilized to deliver media, for example an irrigation liquid, to the proximal end. It is also customary for solids, for example tissue parts or bone particles, or liquids, such as blood or irrigation liquid, to be suctioned off through the interior of the hollow shaft from the operation site. The spacers are designed to allow such flow. For this purpose, the spacers are either provided with suitable openings, or they are designed with radially protruding legs between which sufficient openings are present to allow the flow of such media. In addition, they are designed such that they do not cause unnecessarily high flow resistances to build up.

In another embodiment of the invention, the body and/or the inside wall of the hollow shaft are provided with a material that is favourable in terms of friction.

This can be done by these structural parts being made from the outset from a low-friction material or being subsequently coated with such a material, for example with a polyfluorethylenpolymer material.

This measure has the advantage that, if contact between the body and the inside face of the wall of the hollow shaft were to take place in strongly curved positions, this would be done with low friction.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which:

FIG. 1 shows a side view of a flexible hollow shaft according to the invention in a rectilinear state, FIG. 2 shows a greatly enlarged longitudinal section of the hollow shaft from FIG. 1.

DETAILED DESCRIPTION OF PREFERRED EMBODIMENTS

Figure 3:
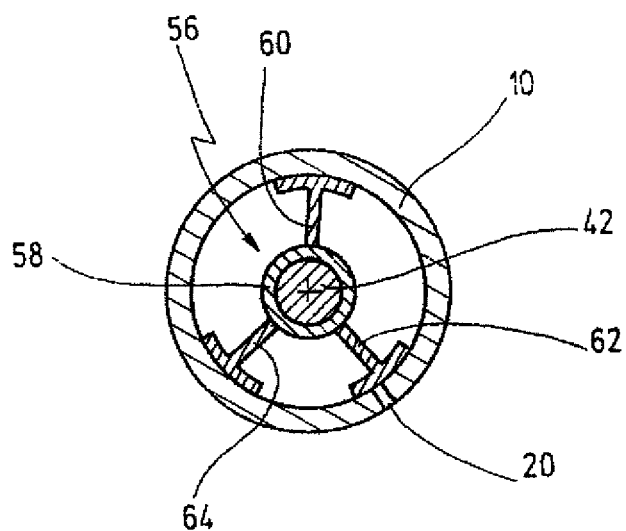
FIG. 3 shows a cross section of a hollow shaft, with a spacer according to a first embodiment mounted on a wire.

A hollow shaft shown in FIGS. 1 and 2 is designated overall by reference number 10.

The hollow shaft 10 has a distal end 12 and a proximal end 14. In the area between distal end 12 and proximal end 14, the body of the hollow shaft 10 is designed as a tube 16 in whose wall 18 numerous cuttings 20 are present.

The cuttings 20 comprise a meandering formation 22 which winds continuously along a helical line. Only a partial segment of the meandering formation 22 is shown in the view in FIG. 1.

At the proximal end 14, the tube is connected to a coupling 24 which serves for connection to a drive mechanism 26 of a medical instrument 28. The hollow shaft 10 can be rotated about its longitudinal axis 29 via the drive mechanism 26, as is indicated by an arrow (see FIG. 2).

The hollow shaft 10 itself is received in a curved shank 30 of the medical instrument 28.

In the views in the figures, the hollow shaft 10 and the curved shank 30 are shown in a rectilinear state, but the meandering formation 22 means the hollow shaft 10 has such flexibility that it can be received in a curved or arc-shaped shank and can be rotated in the curved shank 30 by the drive mechanism 26.

At the distal end 12 a tool is arranged, which, in the illustrative embodiment shown, is a spherical milling head 32.

The milling head 32 merges via a neck 34 and via a step 36 into a peg 38 whose proximal end is connected to a body 40 that extends along the entire length of the tube 16 to the proximal end 14 and is fixedly connected there to the coupling 24.

The body 40 is designed as a wire strand or as a wire 42 which is thus fixedly connected at one end to the peg 38 and at the other end to the coupling 24.

The wire is made of a metal material and is therefore flexible and can follow the curvature movements of the hollow shaft 10. By virtue of its being made of metal material, the wire 42 has high tensile strength and thus forms a means of tension relief.

In other words, the hollow shaft 10 can be extended no further than in the state shown in FIGS. 1 and 2.

Without the central wire 42, this would be possible to a relatively large extent, specifically because of the continuous meandering formation 22 winding in a helical line.

In practical application, the hollow shaft 10 is fixedly connected at its proximal end 14 to the drive mechanism 26 and is thus fixed in respect of its axial position, and is only able to rotate.

Tensile forces, for example when the milling head 32 catches on a bone during an operation, do not lead to longitudinal extension of the hollow shaft 10, as this is prevented by the tension relief provided by means of the inner wire 42.

Up to a certain extent, the wire 42 can also provide for pressure relief. However, if the hollow shaft is very thin, the wire too is very thin, and, particularly when received in the curved shank 30, can provide only slight resistance to compressive forces, since it itself tends to bulge outward.

Therefore, a sleeve 44 is mounted rotatably around the peg 38. The distal end of the sleeve 44 bears on the step 36 of the peg 38. On its outer face 44, the sleeve 44 is provided with a shoulder 46 that acts as a limit stop 48, specifically when this shoulder 46 encounters the corresponding front edge 50 of the shank 30.

When the shoulder 46 comes to bear on this front edge 50, the hollow shaft 10 can be compressed no further, i.e. compressive forces acting on the hollow shaft 10 via the milling head 32 are carried away via the limit stop 48 to the curved shank 30. This therefore relieves the pressure on the hollow shaft 10. By virtue of the fact that the sleeve 44 is rotatable relative to the peg 38, the hollow shaft 10 is able to rotate in the sleeve 44 when, in the case of pressure relief, it comes to lie with its shoulder 46 on the front edge 50 and then sits fixedly in position there.

A connection piece 52 provides for a fixed connection between the tube 16 of the hollow shaft 10 and the peg 38 of the milling head 32.

In the event of strong curvatures, contact may occur between the inside face of the hollow shaft 10 and the wire 42. To allow this to happen in a way that causes the least possible friction, these structural parts can be coated with materials that are favourable in terms of friction, for example with a polyfluorethylenpolymer, or they can be made from the outset from materials that are favourable in terms of friction.

FIG. 3 shows a cross section through the flexible hollow shaft 10, specifically in an area in which a spacer 56 is pushed onto the outer face of the wire 42.

For this purpose, the spacer 56 comprises a sleeve 58 whose clear internal diameter corresponds approximately to the external diameter of the wire 42, such that the spacer 56 can be pushed onto the wire 42. Protruding at uniform radial intervals from the circumference of the sleeve 58 there are three legs 60, 62, 64 that end in contact pads, which are not shown in detail here. The legs 60, 62 and 64 bear on the inside face of the wall 18 of the hollow shaft 10 via these contact pads. This ensures that the wire 42 is kept away from the wall and in a central position in the interior of the hollow shaft 10. Several spacers 56 can be pushed on at axial intervals from one another and are mainly arranged in the middle area along the length of the hollow shaft, that is to say at the locations where the bending is at its greatest, for which reason this spacer 56 cannot be seen in the sectional view in FIG. 2.

The spacer 56 can be produced as an injection-moulded plastic component or can be produced from a metal material.

It will be seen from the cross-sectional view in FIG. 3 that, despite the presence of the spacer 56, media can be conveyed in the axial direction through the hollow shaft 10, whether irrigation media that are to be conveyed from the proximal end to the distal end or media that can be suctioned through the hollow shaft from the distal end to the proximal end, for example irrigation liquid, blood, detached tissue, abraded bone fragments, etc. Finally, the structure is chosen such that the least possible flow resistance is generated by the spacers 56.

Figure 4:
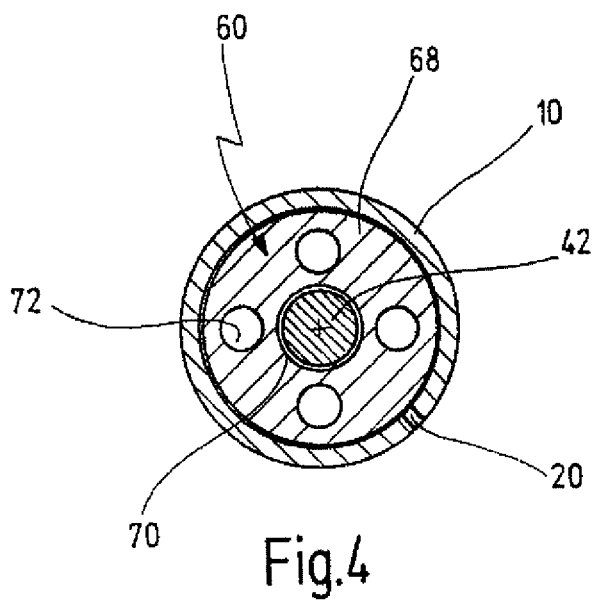
FIG. 4 shows a view comparable to the cross section in FIG. 3, depicting another embodiment of a spacer.

FIG. 4 shows a further illustrative embodiment of a spacer 66 whose body is designed as a disc 68 with a central opening 70. The disc 68 is pushed onto the wire 42 via this central opening 70. The disc 68 is provided with further through-openings 72, in this case four through-openings 72 distributed uniformly about the circumference, in order to allow the aforementioned media to flow through.

What is claimed is:

1. A medical instrument, comprising
   a curved shank comprising a shank limit stop,
   a flexible hollow shaft received in said curved shank,
   said hollow shaft having a wall with cuttings therein such that said hollow shaft can also transmit rotary forces in a curved state,
   said hollow shaft having
      a proximal end for coupling to a drive mechanism of said medical instrument,
      a distal end on which a tool is arranged, said distal end extends beyond a distal end of said curved shank,
      a sleeve mounted rotatably on said distal end of said hollow shaft that comprises a shaft limit stop, and
      a wire extending through an inside of said hollow shaft from said distal end to said proximal end of said shaft, said wire being connected to said distal end and said proximal end, said wire prevents an axial extension of said hollow flexible shaft,
   wherein said shaft limit stop interacts with said shank limit stop,
   wherein said shaft limit stop is at a distance to said shank limit stop, said distance allowing a compression of said hollow shaft until said shaft limit stop abuts said shank limit stop.

2. The medical instrument of claim 1, wherein said tool arranged at said distal end is connected to said proximal end via said wire.

3. The medical instrument of claim 1, wherein said cuttings in said wall of said hollow shaft are designed as a slit winding in a shape of a helical line along said wall.

4. The medical instrument of claim 3, wherein said slit is designed as a slit with a meandering configuration.

5. The medical instrument of claim 1, wherein spacers are provided for keeping said wire inside said hollow shaft at a radial distance from an inner side of said wall of said hollow body.

6. The medical instrument of claim 5, wherein said spacers are designed in that media in an interior of said hollow shaft can be transported in an axial direction across said spacers.

7. The medical instrument of claim 1, wherein said wire is provided with a material that is favourable in terms of friction.

8. The medical instrument of claim 1, wherein an inside of said wall of said hollow shaft is provided with a material that is favourable in terms of friction.

9. The medical instrument of claim 1, wherein said limit stop is designed as a shoulder.

10. The medical instrument of claim 1, wherein said sleeve is mounted in an axial movable manner on said distal end.

11. The flexible shaft of claim 1, wherein said sleeve is mounted in an axially movable manner on said distal end.

* * * * *